United States Patent
Ma et al.

(10) Patent No.: US 10,208,582 B2
(45) Date of Patent: Feb. 19, 2019

(54) FORMATION WATER SALINITY FROM BOREHOLE MEASUREMENTS

(71) Applicant: Saudi Arabian Oil Company, Dhahran (SA)

(72) Inventors: Shouxiang Ma, Dhahran (SA); Nedhal Mohamed Abdullah Al-Musharfi, Dammam (SA); Pablo J. Saldungaray, Al Khobar (SA); Harold Pfutzner, Richmond, TX (US)

(73) Assignees: SAUDI ARABIAN OIL COMPANY, Dhahran (SA); SCHLUMBERGER TECHNOLOGY CORPORATION, Sugar Land, TX (US)

(*) Notice: Subject to any disclaimer, the term of this patent is extended or adjusted under 35 U.S.C. 154(b) by 35 days.

(21) Appl. No.: 15/246,296

(22) Filed: Aug. 24, 2016

(65) Prior Publication Data

US 2018/0058188 A1 Mar. 1, 2018

(51) Int. Cl.
*E21B 47/00* (2012.01)
*G01V 5/10* (2006.01)
*G01N 33/28* (2006.01)

(52) U.S. Cl.
CPC ......... *E21B 47/00* (2013.01); *G01N 33/2823* (2013.01); *G01V 5/102* (2013.01)

(58) Field of Classification Search
CPC .......... G01V 5/102; G01V 5/105; G01V 5/14; G01N 33/2823; E21B 47/00
See application file for complete search history.

(56) References Cited

U.S. PATENT DOCUMENTS

| 4,191,884 A | 3/1980 | Scott |
| 4,287,415 A | 9/1981 | Arnold |
| 4,381,449 A | 4/1983 | Smith, Jr. |

(Continued)

FOREIGN PATENT DOCUMENTS

| GB | 2070764 A | 9/1981 |
| RU | 2262124 C1 | 10/2005 |
| WO | 2009020996 A2 | 2/2009 |
| WO | WO2010039121 A1 | 4/2010 |
| WO | WO2010039122 A1 | 4/2010 |

OTHER PUBLICATIONS

Adolf et al. "Saturation Monitoring with the RST Reservoir Saturation Tool" Oilfield Review, vol. 6, No. 1, pp. 29-39 Elsevier, Jan. 1994.

(Continued)

*Primary Examiner* — Bryan Bui
(74) *Attorney, Agent, or Firm* — Bracewell LLP; Constance G. Rhebergen; Karthika Perumal

(57) ABSTRACT

The present disclosure describes various embodiments related to methods for determining salinity of water in a borehole of a formation and the water in the formation. Various methods may use inelastic and capture gamma-ray spectra obtained from a pulsed neutron logging tool. Various embodiments may use a ratio of chlorine from a capture spectrum to oxygen from an inelastic spectrum for a near and a far detector to calculate apparent salinity ratios for water in a borehole and a formation. From the apparent salinity ratios, a borehole salinity and a formation salinity may be calculated using a tool characterization database and without using formation water saturation for the calculation. Other embodiments may be disclosed or claimed.

10 Claims, 6 Drawing Sheets

(56) References Cited

U.S. PATENT DOCUMENTS

| | | | |
|---|---|---|---|
| 4,454,420 | A | 6/1984 | Smith, Jr. |
| 4,574,193 | A | 3/1986 | Arnold et al. |
| 4,937,446 | A | 6/1990 | McKeon et al. |
| 4,978,851 | A | 12/1990 | Youmans |
| 5,105,080 | A | 4/1992 | Stoller et al. |
| 5,374,823 | A | 12/1994 | Odom |
| 6,207,953 | B1 | 3/2001 | Wilson |
| 7,566,869 | B2 | 7/2009 | Riley et al. |
| 7,791,017 | B2 | 9/2010 | Stephenson et al. |
| 7,937,222 | B2 | 5/2011 | Donadille et al. |
| 8,441,269 | B2 | 5/2013 | Minh et al. |
| 8,849,573 | B2 | 9/2014 | Zhang et al. |
| 9,568,638 | B2 * | 2/2017 | Fitzgerald .............. G01V 5/101 |
| 2007/0255500 | A1 | 11/2007 | Pita et al. |
| 2010/0327154 | A1 | 12/2010 | Vaeth et al. |
| 2014/0343857 | A1 | 11/2014 | Pfutzner et al. |

OTHER PUBLICATIONS

Albertin et al. "The Many Facets of Pulsed Neutron Cased-Hole Logging" Oilfield Review, vol. 8, No. 2, pp. 28-41, Elsevier, Summer 1996.

Al-Sunbul, et al. "Quantifying Remaining Oil by Use of Slimhole Resistivity Measurement in Mixed Salinity Environments—A Pilot Field Test", paper SPE 97489, Dec. 2005, pp. 1-9.

Chardac, et al. "In search of saturation" Middle East Well Evaluation Review, No. 17 (1996) pp. 22-37.

Eyvazzadeh et al. "Modern Carbon/Oxygen Logging Methodologies: Comparing Hydrocarbon Saturation Determination Techniques," SPE 90339, Sep. 2004, pp. 1-14.

He, et al. "A New Chlorine Logging Tool: Application in the Oilfield Development With High Salinity Formation Water." (1997). (pp. 1-9).

International Search Report and Written Opinion for International Application No. PCT/US2012/055680; International Filing Date Sep. 16, 2012; dated Dec. 20, 2012 (pp. 1-5).

Ma, et al. "Cased-Hole Reservoir Saturation Monitoring in Mixed-Salinity Environments—A New Integrated Approach," paper SPE 92426, Mar. 2005, pp. 1-10.

Ma, et al. "Resolving the Mixed Salinity Challenges with a Methodology Developed from Pulsed Neutron Capture Gamma Ray Spectral Measurements", SPE Annual Tech Conference & Exhibition, Oct. 27-29, The Netherlands, Publication Date: 2014. (pp. 1-12).

Plasek, et al. "Improved Pulsed Neutron Capture Logging with Slim Carbon-Oxygen Tools: Methodology," SPE 30598, Oct. 1995, pp. 729-743.

Roscoe, et al. "A New Through-Tubing Oil-Saturation Measurement System," SPE 21413, Nov. 1991, pp. 659-668.

* cited by examiner

FORMATION WATER SALINITY FROM BOREHOLE MEASUREMENTS

FIELD

Embodiments of the present disclosure generally relate to the field of downhole measurements in a borehole for hydrocarbon production. More specifically, embodiments of the present disclosure relate to methods and systems for determining borehole and formation water salinity from pulsed neutron gamma-ray spectroscopy measurements in a borehole.

BACKGROUND

Hydrocarbons may be accompanied by water in underground rock formations. Such water typically may have a high concentration of dissolved salt. After disturbance of a formation by hydrocarbon production operations, the water in the formation may have a variable concentration of dissolved salt. The variation may be over time and location within the formation. This variation may result from the mixing of various water containing fluids used during production with each other and with the water in the formation.

Knowledge of the salt concentration, typically referred to as salinity, in the water of a formation is useful in the process for estimating the volume of hydrocarbons in the formation and thereby in managing production. A salinity measurement is needed because some instruments used for performing downhole measurements in a formation are sensitive to salinity. For example, an instrument may not be able to provide accurate estimates of the water and hydrocarbon fractions without knowledge of salinity. An example of an instrument sensitive to salinity is a borehole resistivity sonde, which is used to measure electrical resistivity of fluid in the pores of a rock. From the resistivity measurement, the fraction of water within pores may be determined. However, since resistivity is sensitive to salinity, knowledge of the water salinity is necessary to compute an accurate estimate of the water fraction in the pores. Since the salinity may vary over time and depth within a formation during various stages of hydrocarbon production, an accurate downhole measurement of salinity is needed over time and as a function of depth within a formation in order to optimize hydrocarbon production.

SUMMARY

Various embodiments disclosed may relate to methods for calculating borehole and formation water salinity based on a relative concentration of chlorine (Cl) to oxygen (O) measured by two downhole gamma ray spectrometers (gamma ray detectors) at different spacing from a pulsed neutron source.

In various embodiments of a method for determining salinity of water in a borehole of a formation and the water in the formation, the method may comprise receiving, by a computer, a pulsed neutron logging (PNL) tool data set generated by a PNL tool, the data set obtained from a borehole of a formation and including a near detector gamma-ray spectra set and a far detector gamma-ray spectra set, wherein the near detector gamma-ray spectra set includes a near inelastic spectrum and a near capture spectrum, and the far detector gamma-ray spectra set includes a far inelastic spectrum and a far capture spectrum; calculating, by the computer using a standard elements database and a data regression method, a first set of coefficients of elements for the near inelastic spectrum, a second set of coefficients of elements for the near capture spectrum, a third set of coefficients for the far inelastic spectrum, and a fourth set of coefficients for the far capture spectrum, wherein the first, second, third, and fourth sets of coefficients of the elements indicate relative amounts of the elements contributing to the corresponding spectrum; calculating, by the computer, a near detector salinity ratio ($SRAT_{Near}$) and a far detector salinity ratio ($SRAT_{Far}$), wherein the near detector salinity ratio is equal to a ratio of a coefficient for chlorine from the second set of coefficients to a coefficient for oxygen from the first set of coefficients, and the far detector salinity ratio is equal to a ratio of a coefficient for chlorine from the fourth set of coefficients to a coefficient for oxygen from the third set of coefficients; calculating, by the computer using a PNL tool characterization database, a near detector apparent salinity ratio using the near detector salinity ratio, and a far detector apparent salinity ratio using the far detector salinity ratio; and calculating, by the computer, a borehole salinity and a formation salinity using the near detector apparent salinity ratio and the far detector apparent salinity ratio and the PNL tool characterization database, wherein calculating of the borehole salinity and the formation water salinity is without using a water saturation value of the formation.

In various embodiments of the method for determining salinity of water in a borehole of the formation and the water in the formation, the method may further include a PNL tool embodiment, wherein the PNL tool may have a far detector and a near detector, wherein the far detector may be to detect gamma rays predominantly from the formation and the near detector may be to detect gamma-rays predominantly from the borehole, wherein the near inelastic spectrum and the far inelastic spectrum may be captured in a first timing window of zero to 20 microseconds after initiation of a neutron pulse of 20 microseconds by a neutron source of the PNL tool and each spectrum may be corrected by subtracting a fraction of mid-timing spectra from a second timing window of 20 to 40 microseconds captured at the near and far detectors respectively, wherein the fraction may be 10 to 30 percent, wherein the near capture spectrum and the far capture spectrum may be captured in a third timing window of 40 to 100 microseconds.

In various embodiments of the method for determining salinity of water in a borehole of the formation and the water in the formation, the method may further include one or more of a standard elements database embodiment and the PNL tool embodiment, wherein the standard elements database embodiment comprises a standard elements database that includes an inelastic standard elements database including oxygen and elements selected from the group consisting of carbon, hydrogen, calcium, silicon, magnesium, sulfur, and iron, and combinations thereof, and a capture standard elements database including chlorine and elements selected from the group consisting of iron, silicon, titanium, calcium, sulfur, hydrogen, and gadolinium, and combinations thereof.

In various embodiments of the method for determining salinity of water in a borehole of the formation and the water in the formation, the method may further include one or more of a regression embodiment, the standard elements database embodiment, and the PNL tool embodiment in any combination, wherein the regression embodiment comprises the first, second, third, and fourth sets of coefficients of the elements are determined by linear regression analysis of the respective spectra as a linear combination of elements from the standard elements database.

In various embodiments of the method for determining salinity of water in a borehole of the formation and the water in the formation, the method may further include one or more of a normalizing embodiment, the regression embodiment, the standard elements database embodiment, and the PNL tool embodiment in any combination, wherein the normalizing embodiment comprises the far inelastic spectrum, near inelastic spectrum, far capture spectrum, and near capture spectrum each are normalized to a mean neutron output before calculating the respective coefficients.

In various embodiments of the method for determining salinity of water in a borehole of the formation and the water in the formation, the method may further include one or more of a calculation embodiment, the normalizing embodiment, the regression embodiment, the standard elements database embodiment, and the PNL tool embodiment in any combination, wherein the calculation embodiment comprises the near detector apparent salinity ratio ($ASAL_{Near}$) is calculated via $ASAL_{Near}=C_{Near}*(SRAT_{Near}/(\alpha_{Near}+SRAT_{Near})$ and the far detector apparent salinity ratio ($ASAL_{Far}$) is calculated via $ASAL_{Far}=C_{Far}*(SRAT_{Far}(\alpha_{Far}+SRAT_{Far})$, wherein $C_{Near}$, $\alpha_{Near}$, $C_{Far}$, $\alpha_{Far}$ are constants for the near and far detector respectively of the PNL tool and are determined by characterization of the PNL tool by fitting laboratory generated data between $ASAL_{Near}$ and $SRAT_{Near}$ and between $ASAL_{Far}$ and $SRAT_{Far}$, by varying borehole and formation properties.

In various embodiments of the method for determining salinity of water in a borehole of the formation and the water in the formation, the method may further include one or more of a database embodiment, the calculation embodiment, the normalizing embodiment, the regression embodiment, the standard elements database embodiment, and the PNL tool embodiment in any combination, wherein the database embodiment comprises the borehole salinity and the formation salinity are obtained from the PNL tool characterization database using the near detector apparent salinity and the far detector apparent salinity and data from the database matching the borehole and the formation.

In various embodiments of the method for determining salinity of water in a borehole of the formation and the water in the formation, the method may further include one or more of a cross plot embodiment, the calculation embodiment, the normalizing embodiment, the regression embodiment, the standard elements database embodiment, and the PNL tool embodiment in any combination, wherein the cross plot embodiment comprises the borehole salinity and the formation salinity are determined from a cross plot of far detector apparent salinity ratio versus near detector apparent salinity ratio, wherein the cross plot forms a quadrilateral and the borehole salinity and formation salinity are determined from the quadrilateral.

BRIEF DESCRIPTION OF THE DRAWINGS

Embodiments of the present disclosure will be readily understood after a review of the following detailed description and the accompanying drawings. To facilitate the detailed description, like reference numerals designate like structural elements in the drawings. Embodiments are illustrated by way of example and not by way of limitation in the figures of the accompanying drawings.

DETAILED DESCRIPTION

Figure 1:
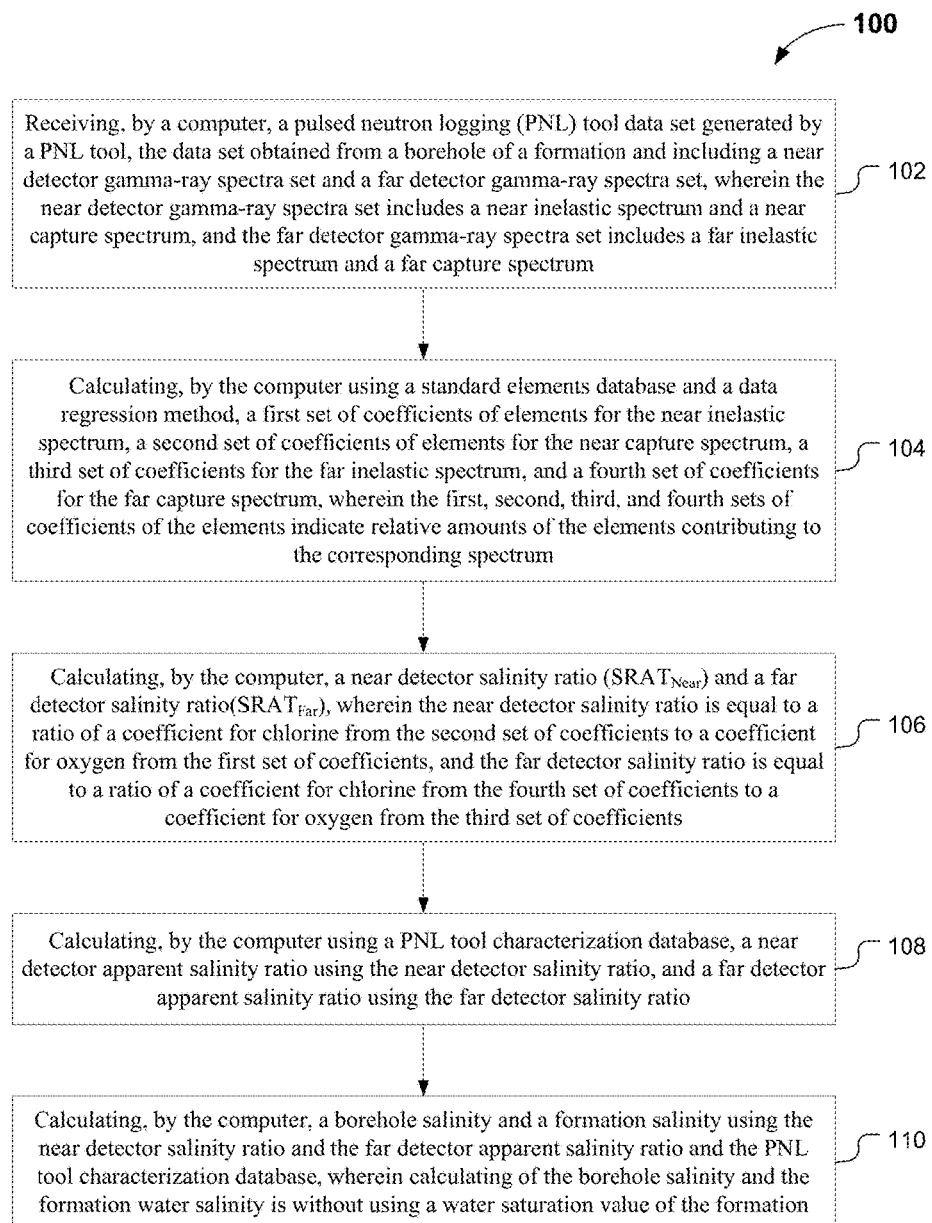
FIG. 1 schematically illustrates a method for determining salinity of water in a borehole and a formation, in accordance with various embodiments.

Embodiments of the present disclosure describe apparatuses and methods for determining borehole and formation water salinity from pulsed neutron gamma-ray spectroscopy measurements in a borehole. In the following description, various aspects of the illustrative implementations are described using terms commonly employed by those skilled in the art to convey the substance of their work to others skilled in the art. However, those skilled in the art will understand that embodiments of the disclosure may be practiced with only some of the described aspects. For purposes of explanation, specific numbers, materials, and configurations are set forth in order to provide a thorough understanding of the illustrative implementations. However, those skilled in the art will understand that embodiments of the present disclosure may be practiced without the specific details. In other instances, well-known features are omitted or simplified in order not to obscure the illustrative implementations.

In the following detailed description, reference is made to the accompanying drawings that form a part of the disclosure, where like numerals designate like parts throughout, and in which is shown by way of illustration embodiments in which the subject matter of the present disclosure may be practiced. Other embodiments may be utilized, and structural or logical changes may be made without departing from the scope of the disclosure. Therefore, the following detailed description is not to be taken in a limiting sense, and the scope of embodiments is defined by the appended claims and their equivalents.

In various embodiments, pulsed neutron gamma-ray spectroscopy measurements may be performed in a borehole of a formation using a pulsed neutron logging (PNL) tool. PNL tools are commonly used in the oil and gas exploration industry for logging information regarding a formation and borehole. Generally, PNL tools may be used to perform measurements in a borehole to obtain information related to composition of the formation and borehole to optimize oil production. In various embodiments, selected portions of a PNL downhole measurement data set may be used in methods described in this disclosure for determining salinity of water in a borehole and in a formation. A person having ordinary skill in the art will understand that commercial PNL tools are available from various manufacturers and may be used for collection of data that may be input into various embodiments described in this disclosure for calculation of salinity of a formation and a borehole. Additionally, a person having ordinary skill in the art will understand that there are literature documents that describe PNL tools and their operation, including the data that may be obtained from PNL tools. Therefore, the various PNL tools and the operation of those tools is understood by a person having ordinary skill in the art, including methods for characterization of various hydrocarbon containing formations using PNL tools.

Generally, a PNL tool for use in various embodiments described in this disclosure may include a high energy pulsed neutron source and at least two gamma-ray detectors. A PNL tool may be designed to have one of the detectors to detect gamma-rays predominantly originating from the borehole, and the other detector to detect gamma-rays predominantly originating from the formation. Positioning or shielding may be design features of a PNL tool used to control whether a detector more preferentially detects gamma-rays from the borehole or the formation. For example, the detectors may be spaced at different distances from the neutron source and may be positioned differently to allow one detector to preferentially detect gamma-rays from the borehole and the other detector to preferentially detect gamma-rays from the formation. Additionally, specific types of shielding may be used in a PNL tool for each detector in order to make a detector sensitive to certain aspects of the borehole or formation. A detector that is nearer to the pulsed neutron source and detects gamma-rays mostly from a borehole generally is referred to as a near detector. A detector that is farther from the pulsed neutron source and detects gamma-rays mostly from a formation is generally referred to as a far detector.

In various embodiments, a PNL tool may be characterized in a laboratory with respect to selected parameters for various formation and borehole conditions. Characterization of a PNL tool is to determine responses at the far detector and near detector under the various formation and borehole conditions. In other words, by systematically varying formation and borehole conditions, responses by the far and near detectors may be correlated to the various formation and borehole conditions. In various embodiments, a PNL tool may be characterized by computer simulation, where selected characteristics of the PNL tool form a portion of the simulation parameters in order to develop correlations between the various formation and borehole conditions and responses at the far and near detectors of the PNL tool. In various embodiments, a combination of laboratory testing and computer simulation may be used to develop a correlation between the various formation and borehole conditions and responses at the far and near detectors. A person having ordinary skill in the art understands that PNL tools are to be characterized in a laboratory, by computer simulation, or by laboratory and computer simulation in order to obtain a correlation of the responses at the far and near detectors to the various formation and borehole conditions.

The various formation and borehole conditions used in a laboratory or in a computer simulation may be selected to bracket the conditions that may be found in various field situations of formation and borehole conditions. By bracketing expected field conditions, the correlations may be used to calculate, by interpolation or extrapolation for example, results of field responses of far and near detectors. If a field situation of formation and borehole conditions lies outside a bracket, an extrapolation may be performed to determine field responses of far and near detectors.

A detector response of a PNL tool may be referred to as a gamma-ray spectrum. A gamma-ray spectrum is a histogram of gamma-ray energy value versus counts at a specific energy value. A gamma-ray spectrum generally is a function of the elements emitting the gamma-rays as a result of neutron bombardment from a high energy neutron source in a PNL tool. A gamma-ray spectrum may be influenced by various formation and borehole conditions. These conditions may include the elements that are present in addition to formation porosity, lithology, and salinity, and borehole diameter, casing properties, and fluid in the borehole, as well as hydrocarbon saturation. Hydrogen Index of the hydrocarbon may be an additional parameter. Formation lithology may influence a gamma-ray spectrum. Properties of formation fluids that may be an influence may include whether the fluid includes oil, water, and/or gas, as well as the composition of the oil, water, and/or gas. If a borehole is cased, properties of such cased boreholes may be an influence. For a cased borehole, these properties may include inside and outside diameter of a casing, the composition of a casing, the eccentricity of a casing, and the properties and composition of a cement between a casing and a borehole.

The laboratory experiments or computer simulations for characterizing a PNL tool, as described previously, may be performed to develop a correlation between an elemental yield calculated from a gamma-ray spectrum with the various parameters for a formation and a borehole. In other words, since the conditions (amounts and distribution) of an experiment or simulation for particular elements are known, correlations may be developed to correct for the impact of changes of the variables. For example, if the amount of a selected element is kept constant, then other variables may be changed to develop a correlation between the variables and the yield of an element calculated from a gamma-ray spectrum. A database of PNL tool responses to the various properties may be generated and used to correct for different downhole conditions related to the various properties for a specific downhole PNL measurement.

PNL tools may be operated to generate a pulse of neutrons with measurement of a gamma-ray response by the detectors over certain timeframes from when the pulse of neutrons started. A pulse of neutrons may be for 20 microseconds, followed by a period of no neutron emissions for 80 microseconds, providing a period of 100 microseconds for the pulse and no emissions timeframe. In other words, a cycle time may be 100 microseconds for pulse and measurements. Measurements of gamma-rays emitted by the borehole and formation after neutron bombardment may be during the entire 100 microsecond period or may be during selected time windows within the 100 microsecond period. For example, a detector may be programmed to capture gamma-ray spectra during a timeframe of about 0 to 20 microseconds, as measured from the starting time of a neutron pulse, to obtain spectra comprised of predominantly gamma-rays from fast neutron inelastic collisions. Such spectra may be referred to as inelastic spectra. In contrast, a detector may be programmed to capture gamma-ray spectra during a timeframe of about 40 to 100 microseconds to obtain spectra comprised of predominantly gamma-rays from thermal neutron capture collisions. Such spectra may be referred to as capture spectra. Inelastic spectra collected during a 0 to 20 microsecond period may be corrected for capture spectra by subtracting a response from a 20 to 40 microsecond period from the 0 to 20 microsecond period using a scaling factor. The scaling factor may be 10 to 30%. In other words, to obtain corrected inelastic spectra, the spectra from the 20 to 40 microsecond window are multiplied by the scaling factor and then subtracted from the spectra from the 0 to 20 microsecond window.

A gamma-ray spectrum obtained using a PNL tool generally relates to the composition of the borehole and formation but may be influenced by certain properties of the borehole and the formation, as described previously. However, a gamma-ray spectrum may be normalized, and specific ratios of elements may be calculated from the normalized spectrum. For example, a common elemental ratio used in PNL tool analysis of a hydrocarbon formation is the carbon to oxygen ratio. This ratio may be referred to as C/O logging and is understood by a person having ordinary skill in the art to be useful for understanding reservoir conditions, within certain limitations. A C/O log is generated from an inelastic spectrum. Capture spectrum data, combined or not with inelastic spectrum data, may be used to obtain formation mineralogy information and correct for lithology effects in the C/O ratios.

FIG. 1 schematically illustrates a method 100 for determining salinity of water in a borehole and a formation, in accordance with various embodiments.

At 102 of method 100, the method 100 may include receiving, by a computer, a pulsed neutron logging (PNL) tool data set generated by a PNL tool, the data set obtained from a borehole of a formation and including a near detector gamma-ray spectra set and a far detector gamma-ray spectra set, wherein the near detector gamma-ray spectra set includes a near inelastic spectrum and a near capture spectrum, and the far detector gamma-ray spectra set includes a far inelastic spectrum and a far capture spectrum.

The computer may be any type of computer capable of performing the methods described in this disclosure, including for example a mainframe computer, a desktop computer, a laptop computer, or a mobile computing device. The computer may receive the data set from a wireless connection, a wired connection, or from any type of memory storage or disk. The computer may receive the data set by retrieving the data set from a memory coupled to the computer or a memory coupled to a second computer. A memory may be any type of memory device including disk drives, RAM, and flash memory, for example.

The PNL tool may include a far detector and a near detector for detecting gamma-rays. The far detector may detect gamma-rays predominantly emitted by the formation. The near detector may detect gamma-rays predominantly from the borehole. The gamma-rays may be emitted by the borehole and the formation in response to a neutron pulse from a high energy neutron source of the PNL tool.

The near inelastic spectrum and the far inelastic spectrum may be captured in a first timing window of approximately zero to 20 microseconds after initiation of a neutron pulse of 20 microseconds by the neutron source of the PNL tool.

The near inelastic spectrum may be a corrected inelastic spectrum, where a fraction of a near mid-timing spectrum from a second timing window of 20 to 40 microseconds may be captured by the near detector and then subtracted from the spectrum captured at the near detector in the zero to 20 microsecond timing window to provide the resulting near net inelastic spectrum. Without being bound by theory, the subtracted spectrum from the second timing window may be to at least partially account for gamma-rays resulting from capture interactions. The amount of the spectrum from the second timing window subtracted may be a fractional amount of approximately 10 to 30 percent.

The far inelastic spectrum may be a corrected inelastic spectrum where a fraction of a near mid-timing spectrum from a second timing window of 20 to 40 microseconds may be captured by the far detector and then subtracted from the spectrum captured at the far detector in the zero to 20 microsecond timing window to provide the resulting far net inelastic spectrum. Without being bound by theory, the subtracted spectrum from the second timing window may be to at least partially account for gamma-rays resulting from capture interactions. The amount of the spectrum from the second timing window subtracted may be a fractional amount of approximately 10 to 30 percent. The near capture spectrum and the far capture spectrum may be captured in a third timing window of 40 to 100 microseconds.

At 104 of method 100, the method 100 may include calculating, by the computer using a standard elements database and a data regression method, a first set of coefficients of elements for the near inelastic spectrum, a second set of coefficients of elements for the near capture spectrum, a third set of coefficients for the far inelastic spectrum, and a fourth set of coefficients for the far capture spectrum, wherein the first, second, third, and fourth sets of coefficients of the elements may indicate relative amounts of the elements contributing to the corresponding spectrum.

The standard elements database may include an inelastic standard elements database including oxygen and elements selected from the group consisting of carbon, hydrogen, calcium, silicon, magnesium, sulfur, and iron, and combinations thereof, and a capture standard elements database including chlorine and elements selected from the group consisting of iron, silicon, titanium, calcium, sulfur, hydrogen, and gadolinium, and combinations thereof.

The standard elements database may be specific to the design of the PNL tool and related to the elements present and emitting gamma-rays in response to neutron bombardment via a neutron pulse. The inelastic standard elements database may be represented as a plot of relative gamma-ray counts versus energy level in million electron volts (MeV) of the gamma-rays. The inelastic standard elements database may include a background component of inelastic gamma-rays. The capture standard elements database may be represented as a plot of relative gamma-ray counts versus energy level in million electron volts (MeV) of the gamma-rays. The capture standard elements database may include a background component of inelastic gamma-rays.

The first, second, third, and fourth sets of coefficients of the elements may be determined by linear regression analysis of the respective spectra as a linear combination of elements from the standard elements database. The far inelastic spectrum, near inelastic spectrum, far capture spectrum, and near capture spectrum each may be normalized to a mean neutron output before calculating the respective first, second, third, and fourth sets of coefficients of the elements.

At 106 of method 100, the method 100 may include calculating, by the computer, a near detector salinity ratio ($SRAT_{Near}$) and a far detector salinity ratio ($SRAT_{Far}$), wherein the $SRAT_{Near}$ may be equal to a ratio of a coefficient for chlorine from the second set of coefficients to a coefficient for oxygen from the first set of coefficients, and the far detector salinity ratio may be equal to a ratio of a coefficient for chlorine from the fourth set of coefficients to a coefficient for oxygen from the third set of coefficients.

At 108 of method 100, the method 100 may include calculating, by the computer using a PNL tool characterization database, a near detector apparent salinity ratio using the near detector salinity ratio, and a far detector apparent salinity ratio using the far detector salinity ratio. The near detector apparent salinity ratio ($ASAL_{Near}$) may be calculated by Equation 1.

$$ASAL_{Near} = C_{Near} * (SRAT_{Near}/(\alpha_{Near} + SRAT_{Near}))\quad\text{Equation [1]}$$

The far detector apparent salinity ratio ($ASAL_{Far}$) may be calculated by Equation 2.

$$ASAL_{Far} = C_{Far} * (SRAT_{Far}/(\alpha_{Far} + SRAT_{Far}))\quad\text{Equation [2]}$$

The constants $C_{Near}$, $\alpha_{Near}$, $C_{Far}$, $\alpha_{Far}$ may be constants for the near and far detector respectively of the PNL tool. These constants may be determined by characterization of the PNL tool by fitting laboratory generated data between $ASAL_{Near}$ and $SRAT_{Near}$ and between $ASAL_{Far}$ and $SRAT_{Far}$, by varying borehole and formation properties.

At 110 of method 100, the method 100 may include calculating, by the computer, a borehole salinity and a formation salinity using the near detector apparent salinity ratio and the far detector apparent salinity ratio and the PNL tool characterization database. The method may include calculating the borehole water salinity without using an oil holdup value ($Y_o$) of the borehole and the formation water salinity without using a water saturation value ($S_w$) of the formation. Not having to use $Y_o$ and $S_w$ in the calculation may simplify calculating the borehole and formation salinities.

In various embodiments, the near detector apparent salinity ratio and the far detector apparent salinity ratio may be mapped onto the PNL tool characterization database to match the borehole and formation parameters within the PNL tool characterization database to the borehole and formation parameters of the specific borehole and formation. The mapping may include interpolation of data values within the database. In various embodiments, the PNL tool characterization database may include various polynomial equations that fit the data of the database between borehole salinity and formation salinity to near detector apparent salinity and far detector apparent salinity for selected borehole and formation parameters.

In various embodiments, the borehole salinity and the formation salinity may be determined from a cross plot of the far detector apparent salinity ratio versus the near detector apparent salinity ratio, wherein the cross plot forms a quadrilateral and the borehole salinity and formation salinity may be determined from the quadrilateral by mapping the values of the far detector apparent salinity ratio and the near detector apparent salinity ratio to the quadrilateral. The quadrilateral may have as corners salinity of the borehole and formation as zero at a lower left corner, salinity of the borehole and formation at a large value such as 200 parts per thousand (ppk) at the opposite upper right corner, formation salinity at zero and borehole salinity at a large value such as 200 ppk at the lower right corner, and borehole salinity at zero and formation salinity at a large value such as 200 ppk at the upper left corner. The quadrilateral may have intermediate points and lines. The quadrilateral may allow determination of borehole and formation salinity by a simple cross plotting of the near detector apparent salinity ratio and the far detector apparent salinity ratio onto the quadrilateral.

Figure 2:
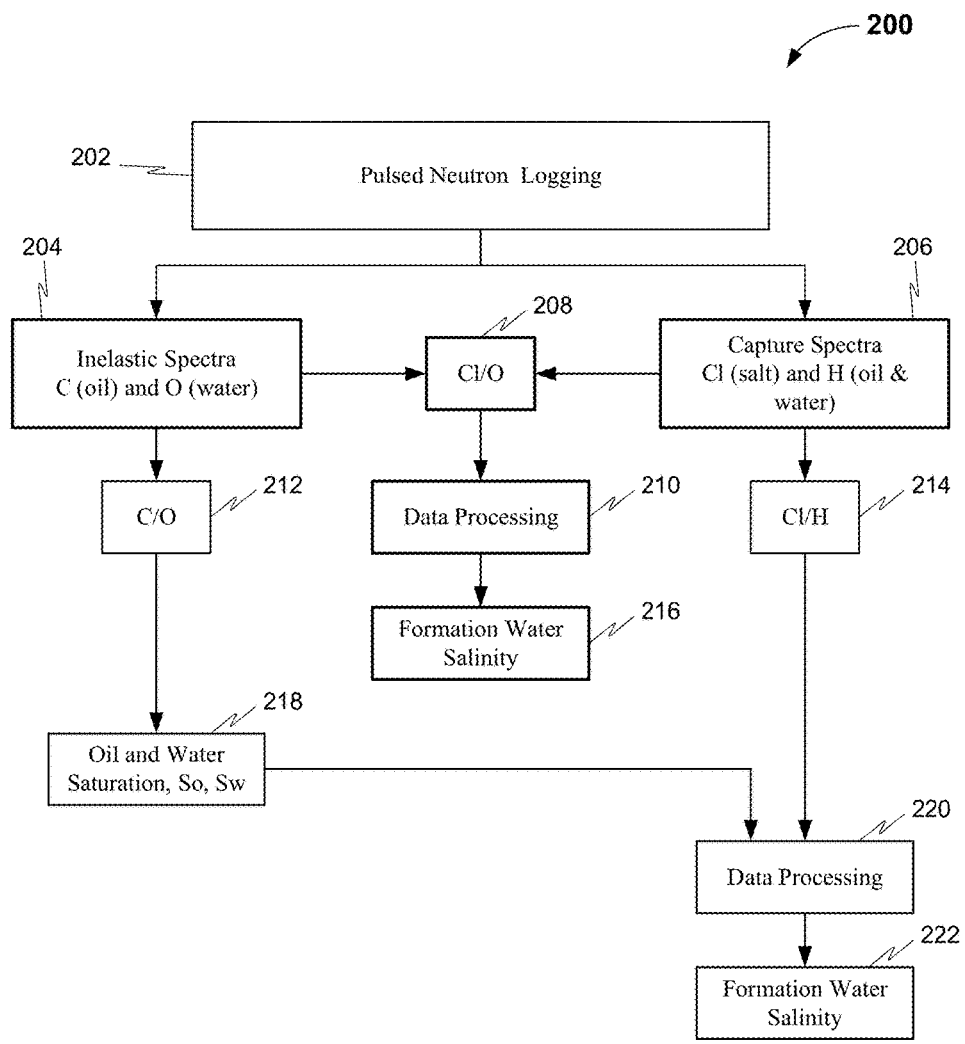
FIG. 2 schematically illustrates a block diagram comparing a method using chlorine and hydrogen spectral data with a water saturation correct for determining formation water salinity in comparison to a method using chlorine and oxygen spectral data without a water saturation correction, in accordance with various embodiments.

FIG. 2 schematically illustrates a block diagram 200 comparing a method using chlorine and hydrogen spectral data with a water saturation correct for determining formation water salinity in comparison to a method using chlorine and oxygen spectral data without a water saturation correction, in accordance with various embodiments.

In the block diagram 200, a pulsed neutron logging (PNL) 202 may be performed using a PNL tool in a borehole of a formation to obtain inelastic spectra 204 and capture spectra 206 at a near and far detector of the PNL tool.

Figure 3:
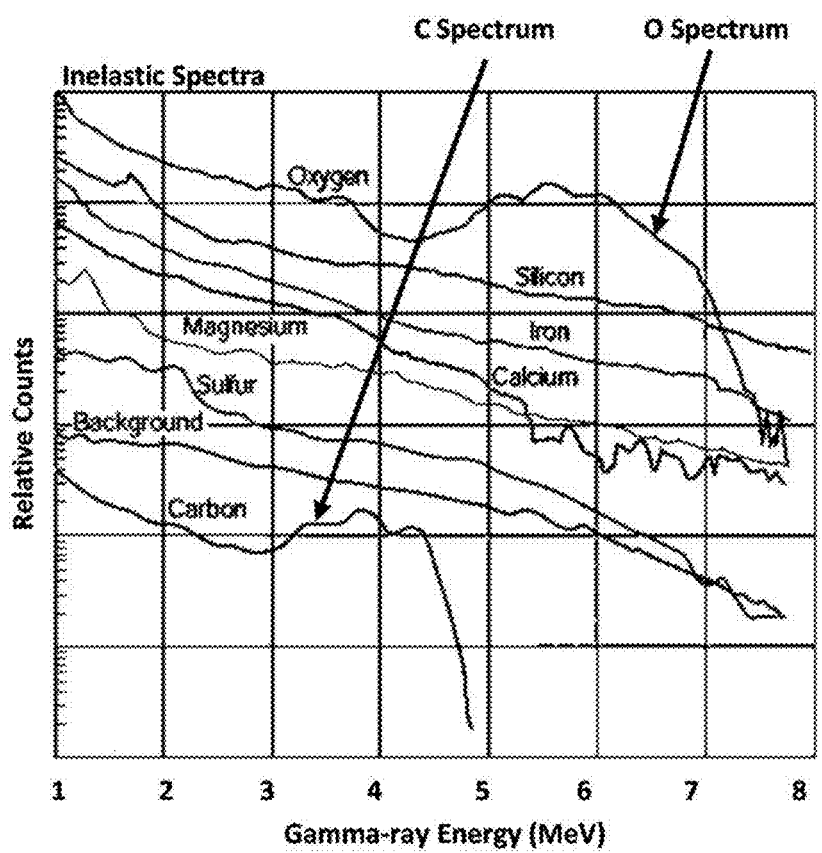
FIG. 3 schematically illustrates a standard inelastic spectra showing various elements found in borehole pulsed nuclear logging tool measurements, in accordance with various embodiments.
Figure 4:
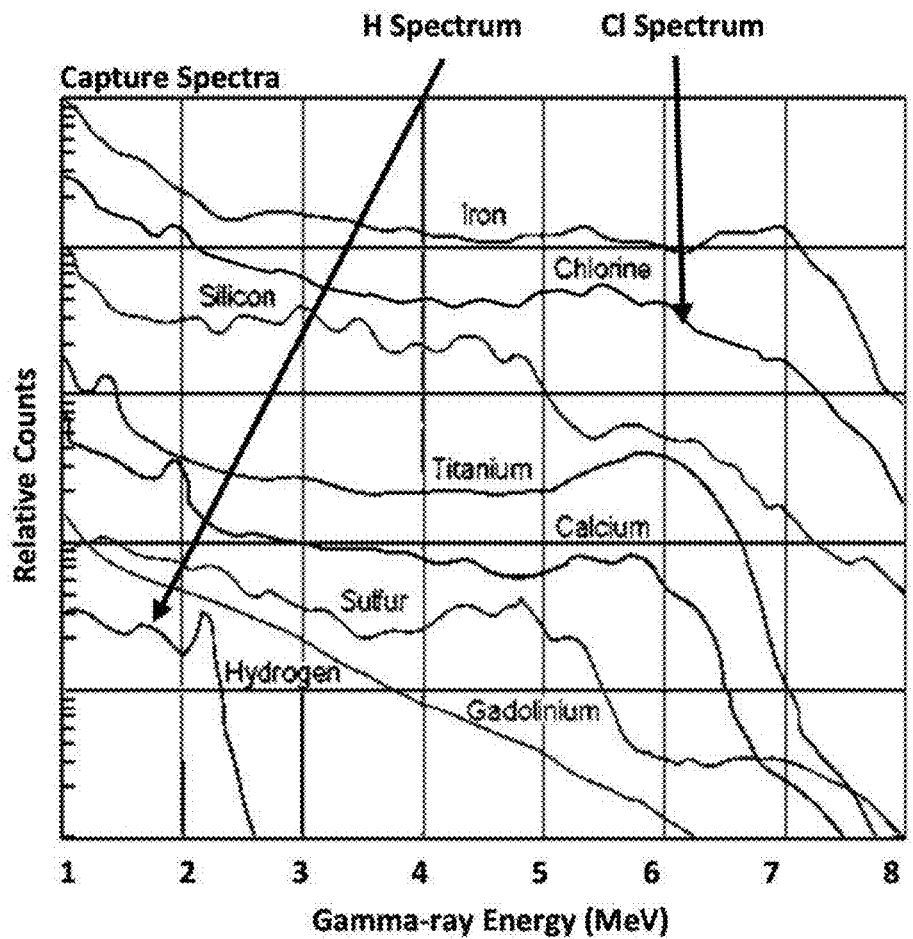
FIG. 4 schematically illustrates a standard capture spectra showing various elements found in borehole pulsed nuclear logging tool measurements, in accordance with various embodiments.

From the inelastic spectra 204, a carbon to oxygen ratio 212 may be obtained by using a standards database of inelastic spectra for various elements, as illustrated in FIG. 3. The standards database may be used to determine coefficients for carbon and oxygen where the coefficients represent relative amounts of carbon and oxygen. The relative amounts may be determined at the near and far detectors. Carbon may be representative of the amount of oil, and oxygen may be representative of the amount of water. From the carbon to oxygen ratio 212, an oil saturation value and a water saturation value 218 may be obtained for the formation. From the capture spectra 206, a chlorine to hydrogen ratio 214 may be obtained by using a standards database of capture spectra for various elements, as illustrated in FIG. 4. The capture spectra standards database may be used to determine coefficients for chlorine and hydrogen where the coefficients represent relative amounts of the elements. The relative amounts may be determined at the near and far detectors. Chlorine may be representative of the amount of salt, and hydrogen may be representative of the amount of water and oil. Using the chlorine to hydrogen ratio 214 and a water saturation value 218, a formation water salinity 222 may be calculated. The water saturation value 218 is necessary to provide a correction to the hydrogen value for the calculation. The various data processing 220 methods may use a database for borehole and formation conditions for the PNL tool, where the PNL tool was previously characterized under various borehole and formation conditions.

In various embodiments, a formation water salinity 216 may be calculated using a capture spectra 206 for chlorine and an inelastic spectra 204 for oxygen, both obtained at the near and far detectors of the PNL tool. The chlorine and oxygen spectra may be used to determine coefficients for chlorine and oxygen representing the relative amounts of salt and water respectively. Data processing 210 may be performed to calculate the formation water salinity. The data processing 210 may include use of a database for characterizing the PNL tool under various borehole and formation conditions. An advantage of this method is that no water saturation value is required as with the chlorine and hydrogen ratio method used for calculating formation water salinity.

FIG. 3 schematically illustrates a standard inelastic spectra showing various elements found in borehole pulsed nuclear logging tool measurements, in accordance with various embodiments. The illustrated standard inelastic spectra are characteristics of the specific elements and are independent from a specific PNL tool. The spectra for the elements of FIG. 3 may be used to determine the relative amounts of elements in an inelastic spectra obtained at a near and far detector of a PNL tool.

FIG. 4 schematically illustrates standard capture spectra showing various elements found in borehole pulsed nuclear logging tool measurements, in accordance with various embodiments. The illustrated standard capture spectra are characteristics of the specific elements and are independent from a specific PNL tool. The spectra for the elements of FIG. 4 may be used to determine the relative amounts of elements in a capture spectra obtained at a near and far detector of a PNL tool.

Figure 5:
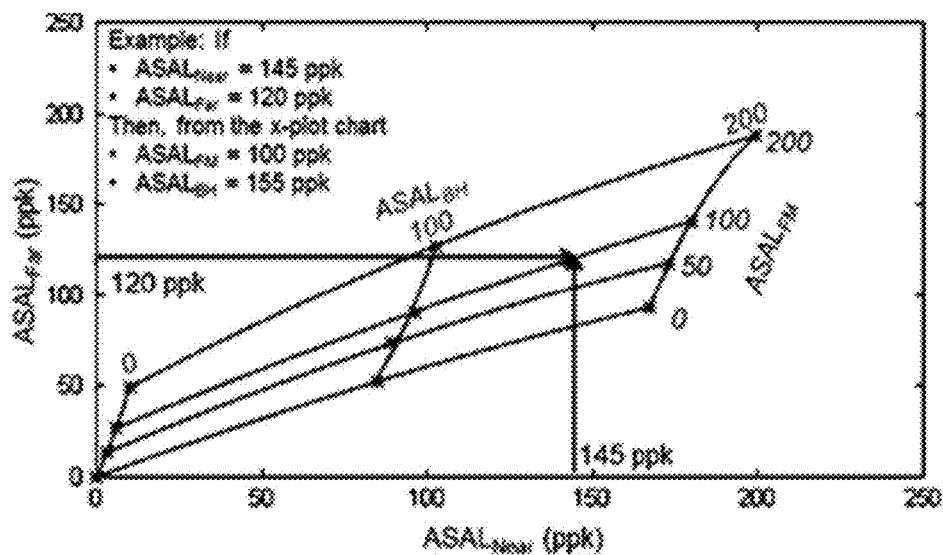
FIG. 5 schematically illustrates a graphical method for determining borehole and formation water salinity using an inelastic and capture spectra standards database for elements and a tool characterization database for a pulsed neutron logging tool, in accordance with various embodiments.

FIG. 5 schematically illustrates a graphical method for determining borehole and formation water salinity using an inelastic and capture spectra standards database for elements and a tool characterization database for a pulsed neutron logging tool, in accordance with various embodiments. In FIG. 5, apparent salinity of a far detector ($ASAL_{Far}$) in parts per thousand (ppk) is plotted against apparent salinity of a near detector ($ASAL_{Near}$) in ppk, where the plot provides a parallelogram bracketing expected values for borehole and formation salinity. The ASAL values may be calculated as illustrated by Equations [1] and [2] and the accompanying description. The lower left corner of the parallelogram represents zero salinity in the borehole and the formation. The upper left corner of the parallelogram represents zero salinity in the formation and 200 ppk in the borehole. The upper right corner of the parallelogram represents 200 ppk salinity in the borehole and formation. The lower right corner of the parallelogram represents zero borehole salinity and 200 ppk formation salinity. The lines along the parallelogram represent constant values of borehole or formation salinity, as the case may be for each salinity value. In the example shown in FIG. 5, the example calculated value of $ASAL_{Near}$ is 145 ppk, and the example calculated value of $ASAL_{Far}$ is 120 ppk. These calculations may be based on using Equations [1] and [2]. The formation water salinity ($ASAL_{FM}$) and the borehole water salinity ($ASAL_{BH}$) may be determined by the intersection of the $ASAL_{Far}$ point with the $ASAL_{Near}$ point, as shown, inside the parallelogram along the constant value lines for $ASAL_{FM}$ and $ASAL_{BH}$. In this example, the value $ASAL_{FM}$ is 100 ppk, and the value of $ASAL_{BH}$ is 155 ppk.

Figure 6:
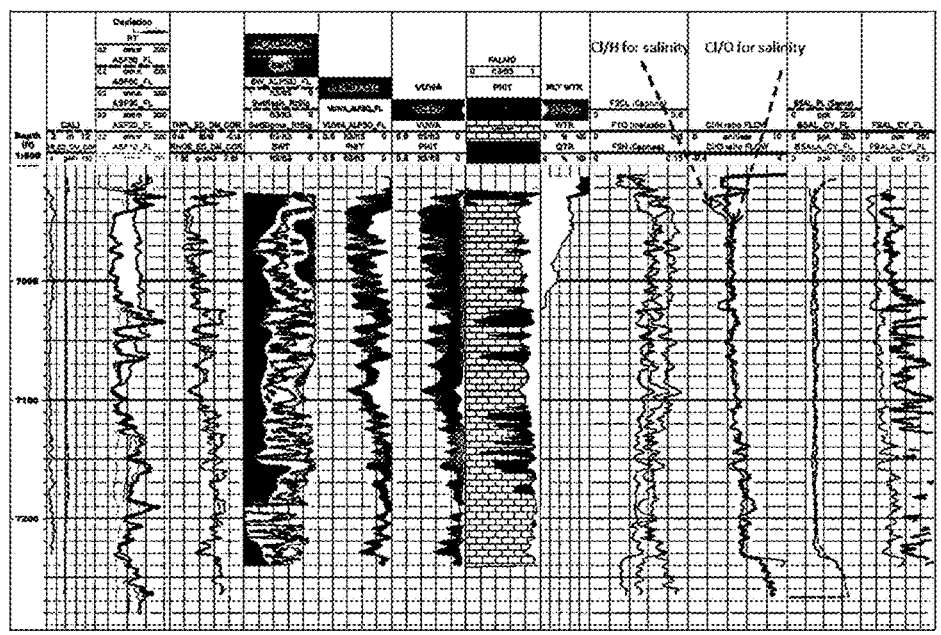
FIG. 6 schematically illustrates a downhole log showing various logs including a comparison of formation water salinity values determined via chlorine and hydrogen with water saturation correction and via chlorine and oxygen without water saturation correction, in accordance with various embodiments.

FIG. 6 schematically illustrates a downhole log showing various logs including a comparison of formation water salinity values determined via chlorine and hydrogen with water saturation correction and via chlorine and oxygen without water saturation correction, in accordance with various embodiments. As can be seen in FIG. 6, the formation water salinity value calculated using chlorine and hydrogen spectra with water saturation correction tracks closely with the formation water salinity value calculated using chlorine and oxygen without water saturation correction. Accordingly, the method using chlorine and oxygen provides an improvement in simplicity of calculating formation water salinity since no correction for water saturation value is needed for the calculation.

What is claimed is:

1. A method for determining salinity of water in a borehole penetrating a formation and water in the formation, comprising:
   lowering a pulsed neutron logging (PNL) tool with a far gamma ray detector and a near gamma ray detector into a borehole penetrating a formation;
   positioning the near gamma ray detector to detect gamma rays predominantly from the borehole and capture a near detector gamma-ray spectra set including a near inelastic spectrum and a near capture spectrum;
   positioning the far gamma ray detector to detect gamma rays predominantly from the formation and capture a far detector gamma-ray spectra set including a far inelastic spectrum and a far capture spectrum;
   receiving, by a computer, a pulsed neutron logging (PNL) tool data set including the near detector gamma-ray spectra set and the far detector gamma-ray spectra set;
   calculating, by the computer using a standard elements database and a data regression method, a first set of coefficients of elements for the near inelastic spectrum, a second set of coefficients of elements for the near capture spectrum, a third set of coefficients for the far inelastic spectrum, and a fourth set of coefficients for the far capture spectrum, wherein the first, second, third, and fourth sets of coefficients of the elements indicate relative amounts of the elements contributing to the corresponding spectrum;
   calculating, by the computer, a near detector salinity ratio ($SRAT_{Near}$) and a far detector salinity ratio ($SRAT_{Far}$), wherein the near detector salinity ratio is equal to a ratio of a coefficient for chlorine from the second set of coefficients to a coefficient for oxygen from the first set of coefficients, and the far detector salinity ratio is equal to a ratio of a coefficient for chlorine from the fourth set of coefficients to a coefficient for oxygen from the third set of coefficients;
   calculating, by the computer, using a PNL tool characterization database, a near detector apparent salinity ratio using the near detector salinity ratio, and a far detector apparent salinity ratio using the far detector salinity ratio; and
   calculating, by the computer, a borehole salinity and a formation salinity using the near detector apparent salinity ratio and the far detector apparent salinity ratio and the PNL tool characterization database, and without using a water saturation value of the formation.

2. The method of claim 1, wherein the near inelastic spectrum and the far inelastic spectrum are captured in a first timing window of zero to 20 microseconds after initiation of a neutron pulse of 20 microseconds by a neutron source of the PNL tool and each spectrum is corrected by subtracting a fraction of mid-timing spectra from a second timing window of 20 to 40 microseconds captured at the near and far detectors respectively, wherein the fraction is 10 to 30 percent, and the near capture spectrum and the far capture spectrum are captured in a third timing window of 40 to 100 microseconds.

3. The method of claim 1, wherein the standard elements database includes an inelastic standard elements database including oxygen and elements selected from the group consisting of carbon, hydrogen, calcium, silicon, magnesium, sulfur, and iron, and combinations thereof, and a capture standard elements database including chlorine and elements selected from the group consisting of iron, silicon, titanium, calcium, sulfur, hydrogen, and gadolinium, and combinations thereof.

4. The method of claim 1, wherein the first, second, third, and fourth sets of coefficients of the elements are determined by linear regression analysis of the respective spectra as a linear combination of elements from the standard elements database.

5. The method of claim 1, wherein the far inelastic spectrum, near inelastic spectrum, far capture spectrum, and near capture spectrum each are normalized to a mean neutron output before calculating the respective coefficients.

6. The method of claim 1, wherein the near detector apparent salinity ratio ($ASAL_{Near}$) is calculated via $ASAL_{Near} = C_{Near} * (SRAT_{Near}/(\alpha_{Near} + SRAT_{Near}))$ and the far detector apparent salinity ratio ($ASAL_{Far}$) is calculated via $ASAL_{Far} = C_{Far} * (SRAT_{Far}/(\alpha_{Far} + SRAT_{Far}))$, wherein $C_{Near}$, $\alpha_{Near}$, $C_{Far}$, $\alpha_{Far}$ are constants for the near and far detector respectively of the PNL tool and are determined by characterization of the PNL tool by fitting laboratory generated data between $ASAL_{Near}$ and $SRAT_{Near}$ and between $ASAL_{Far}$ and $SRAT_{Far}$, by varying borehole and formation properties.

7. The method of claim 1, wherein the borehole salinity and the formation salinity are obtained from the PNL tool characterization database using the near detector apparent salinity and the far detector apparent salinity and data from the database matching the borehole and the formation.

8. The method of claim 1, wherein the borehole salinity and the formation salinity are determined from a cross plot of far detector apparent salinity ratio versus near detector apparent salinity ratio, the cross plot forming a quadrilateral with four endpoints corresponding to: (1) low borehole salinity and low formation salinity, (2) low borehole salinity and high formation salinity, (3) high borehole salinity and high formation salinity, and (4) high borehole salinity and low formation salinity and the borehole salinity and formation salinity are determined from the quadrilateral.

9. The method of claim 8, wherein the high formation salinity is 200 parts per thousand and high borehole salinity is 200 parts per thousand.

10. The method of claim 1, wherein the borehole salinity is determined without using oil hold-up value of the borehole.

* * * * *